United States Patent
Stanley

(10) Patent No.: US 10,758,216 B2
(45) Date of Patent: Sep. 1, 2020

(54) INTERNAL CLOSURE SYSTEMS AND DEVICES

(71) Applicant: Cook Medical Technologies LLC, Bloomington, IN (US)

(72) Inventor: Cleon Stanley, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 14/207,735

(22) Filed: Mar. 13, 2014

(65) Prior Publication Data

US 2014/0277115 A1     Sep. 18, 2014

Related U.S. Application Data

(60) Provisional application No. 61/781,664, filed on Mar. 14, 2013.

(51) Int. Cl.
*A61B 17/00*     (2006.01)

(52) U.S. Cl.
CPC ............. *A61B 17/0057* (2013.01); *A61B 2017/00004* (2013.01); *A61B 2017/00592* (2013.01);
(Continued)

(58) Field of Classification Search
CPC ........... A61B 17/0057; A61B 17/0401; A61B 17/12159; A61B 17/12031; A61B 17/12036; A61B 17/1204; A61B 17/12022; A61B 17/12109; A61B 17/12113; A61B 2017/00592; A61B 2017/0061; A61B 2017/00615; A61B 2017/00619; A61B 2017/00628; A61B 2017/00659; A61B 2017/00641; A61B 2017/00654; A61B 2017/00637; A61B 2017/0417; A61B 2017/042; A61B 2017/0464;
(Continued)

(56) References Cited

U.S. PATENT DOCUMENTS 4,744,364 A     5/1988     Kensey
5,269,809 A     12/1993     Hayhurst et al.
(Continued)

FOREIGN PATENT DOCUMENTS

EP     0 534 696 A1     3/1993
EP     1 169 968 A1     1/2002
(Continued)

OTHER PUBLICATIONS

International Search Report and Written Opinion issued in PCT/US2012/066173, dated Mar. 8, 2013.
(Continued)

*Primary Examiner* — Katherine H Schwiker
(74) *Attorney, Agent, or Firm* — Woodard, Emhardt, Henry, Reeves & Wagner, LLP

(57) ABSTRACT

Among other things, there are shown embodiments of internal members for closure of vascular wall or other bodily openings, particularly useful in closing larger holes (e.g. larger than 10 French). Embodiments create a better seal or meeting with a vascular or other tissue wall by distributing force outward from the center, and/or by including rib, groove or hinge features that allow the internal member, as it is pulled toward tissue, to close the hole and engage tissue more closely or firmly.

15 Claims, 6 Drawing Sheets

(52) U.S. Cl.
CPC .............. *A61B 2017/00628* (2013.01); *A61B 2017/00659* (2013.01)

(58) Field of Classification Search
CPC .... A61B 2017/0057; A61B 2017/0058; A61B 2017/00575; A61B 2017/00601; A61B 2017/00606; A61B 2017/00623; A61B 2017/00632; A61B 2017/00597; A61B 2017/00676; A61B 2017/00496; A61B 2017/0419; A61B 2017/00646; A61B 2017/0065; A61B 2017/00663; A61B 2017/00668; A61B 2017/00672; A61B 17/12168; A61B 17/12172; A61B 17/12177; A61B 2017/00579; A61B 2017/1205; A61B 2017/12095; A61B 2017/12054; A61F 2/06; A61F 2/0063
USPC .......................................... 606/213, 215, 232
See application file for complete search history.

(56) References Cited

U.S. PATENT DOCUMENTS

| | | | |
|---|---|---|---|
| 5,312,435 A | 5/1994 | Nash et al. | |
| 5,343,393 A | 8/1994 | Stack | |
| 5,350,399 A | 9/1994 | Erlebacher et al. | |
| 5,411,520 A | 5/1995 | Nash et al. | |
| 5,531,759 A | 7/1996 | Kensey et al. | |
| 5,545,178 A | 8/1996 | Kensey et al. | |
| 5,620,461 A | 4/1997 | Muijs Van De Moer | |
| 5,662,681 A | 9/1997 | Nash et al. | |
| 5,700,277 A | 12/1997 | Nash et al. | |
| 5,800,436 A | 9/1998 | Lerch | |
| 5,916,236 A | 6/1999 | van de Moer | |
| 6,071,301 A | 6/2000 | Cragg et al. | |
| 6,190,400 B1 | 2/2001 | Van De Moer et al. | |
| 6,425,911 B1 | 7/2002 | Akerfeldt | |
| 6,491,714 B1 | 12/2002 | Bennett | |
| 6,508,828 B1 | 1/2003 | Akerfeldt et al. | |
| 6,537,299 B1* | 3/2003 | Hogendijk ......... A61B 17/0057 606/213 |
| 6,596,013 B2 | 7/2003 | Yang et al. | |
| 6,755,868 B2 | 6/2004 | Rousseau | |
| 6,764,500 B1 | 7/2004 | Muijs Van De Moer et al. | |
| 6,860,895 B1 | 3/2005 | Akerfeldt et al. | |
| 6,921,401 B2 | 7/2005 | Lerch et al. | |
| 6,939,363 B2 | 9/2005 | Akerfeldt | |
| 7,048,710 B1 | 5/2006 | Cragg et al. | |
| 7,169,168 B2 | 1/2007 | Muijs Van De Moer et al. | |
| 7,338,514 B2 | 3/2008 | Wahr et al. | |
| 7,597,705 B2 | 10/2009 | Forsberg et al. | |
| 7,621,937 B2 | 11/2009 | Pipenhagen et al. | |
| 7,658,748 B2 | 2/2010 | Marino et al. | |
| 7,717,929 B2 | 5/2010 | Fallman | |
| 7,875,052 B2 | 1/2011 | Kawaura et al. | |
| 7,931,671 B2 | 4/2011 | Paul et al. | |
| 7,993,367 B2 | 8/2011 | Bagaoisan et al. | |
| 8,105,352 B2 | 1/2012 | Egnelov | |
| 8,257,389 B2 | 9/2012 | Chanduszko et al. | |
| 8,480,709 B2 | 7/2013 | Chanduszko et al. | |
| 8,652,166 B2 | 2/2014 | Akerfeldt | |
| 2002/0019648 A1* | 2/2002 | Akerfeldt ........... A61B 17/0057 606/213 |
| 2003/0181988 A1 | 9/2003 | Rousseau | |
| 2005/0085855 A1 | 4/2005 | Forsberg | |
| 2005/0169974 A1 | 8/2005 | Tenerz | |
| 2005/0283187 A1* | 12/2005 | Longson ............ A61B 17/0057 606/213 |
| 2006/0142797 A1 | 6/2006 | Egnelov | |
| 2006/0206146 A1 | 9/2006 | Tenerz | |
| 2007/0123936 A1 | 5/2007 | Goldin et al. | |
| 2007/0198059 A1 | 8/2007 | Patel et al. | |
| 2008/0071310 A1 | 3/2008 | Hoffman et al. | |
| 2008/0114395 A1 | 5/2008 | Mathisen et al. | |
| 2008/0287986 A1 | 11/2008 | Thor et al. | |
| 2008/0312684 A1 | 12/2008 | Drasler et al. | |
| 2009/0018574 A1 | 1/2009 | Martin | |
| 2009/0054926 A1 | 2/2009 | Pipenhagen et al. | |
| 2009/0088793 A1 | 4/2009 | Bagaoisan et al. | |
| 2009/0112257 A1 | 4/2009 | Preinitz | |
| 2009/0143817 A1 | 6/2009 | Akerfeldt | |
| 2009/0216267 A1 | 8/2009 | Willard et al. | |
| 2009/0234377 A1 | 9/2009 | Mahlin | |
| 2010/0042144 A1 | 2/2010 | Bennett | |
| 2010/0087854 A1 | 4/2010 | Stopek et al. | |
| 2010/0217308 A1 | 8/2010 | Hansen et al. | |
| 2010/0217309 A1 | 8/2010 | Hansen et al. | |
| 2011/0066181 A1 | 3/2011 | Jenson et al. | |
| 2011/0213415 A1* | 9/2011 | McGuckin, Jr. ... A61B 17/0057 606/213 |
| 2011/0288581 A1 | 11/2011 | Paul et al. | |
| 2012/0116447 A1 | 5/2012 | Stanley et al. | |

FOREIGN PATENT DOCUMENTS

| | | |
|---|---|---|
| EP | 1 266 626 A1 | 12/2002 |
| EP | 1 413 255 A1 | 4/2004 |
| EP | 1 440 661 | 7/2004 |
| EP | 2 064 999 A2 | 6/2009 |
| WO | WO 1999/33402 | 7/1999 |
| WO | WO 2000/078226 | 12/2000 |
| WO | WO 2005/063133 A1 | 7/2005 |
| WO | WO 2006/075228 | 7/2006 |
| WO | WO 2007/059243 A1 | 5/2007 |
| WO | WO 2011/146729 A2 | 11/2011 |

OTHER PUBLICATIONS

Written Opinion, PCT/US2011/037173, dated Nov. 17, 2011.
Search Report, PCT/US2011/037173, dated Nov. 17, 2011.

* cited by examiner

INTERNAL CLOSURE SYSTEMS AND DEVICES

This disclosure concerns sealing or anchoring members for use in closing holes through bodily tissue. In particular, there is shown and disclosed embodiments of such members that effectively seal or anchor holes in tissue, such as those in the walls of blood vessels.

BACKGROUND

A number of plugs, seals and other devices are known for covering or closing holes in bodily tissues. In the example of openings through the walls of blood vessels, such as those made for insertion of catheters or other diagnostic or treatment purposes, such devices generally extend across or fill up an opening. Devices such as those disclosed in application Ser. No. 13/111,338, filed on May 19, 2011 and application Ser. No. 13/303,707, filed on Nov. 23, 2011 (both of which are incorporated by reference herein in their entireties) have proven quite effective in closing arteriotomy openings.

However, many currently available closures are designed for relatively small openings, e.g. about 6-10 French. A generally circular anchor or seal can be placed within the vessel and pulled against the inside of the vessel wall. Such devices may be less successful at closing larger openings, e.g. greater than 10 French in size, because of the size and configuration of the opening compared to that of the closure. One problem noted is that closures can evert and be pulled through a large opening when the closure is pulled against a vessel wall. If that happens, an emergency situation may arise, and a different closure will be needed to close the opening. For larger openings, larger domes sealing elements may be used, but as the sealing elements get larger the curvature that needs to be achieved by the closure when they are deployed will be greater. The closure may be less inclined to hug the vessel wall toward its edge, and if not, may become an obstruction to blood flow within the vessel and/or create leakage. Closures designed for larger openings, and that effectively spread force applied to the closure and allow it to hug the vessel wall more closely, are needed.

SUMMARY

Among other things, there is disclosed a vascular closure system that includes an internal member for anchoring or sealing against the inside wall of a blood vessel. The internal member in particular embodiments is at least partially ellipsoidal with a major axis and a minor axis, and having an exterior surface for facing away from the inside wall and an interior surface for facing the inside wall, wherein in an initial unstressed configuration the exterior surface is convex and the interior surface is concave. A plurality of elongated members is fixed to the interior surface of the internal member, with the elongated members being arranged symmetrically across the major axis and being non-orthogonal to the interior surface at a point at which the respective elongated members engage the internal member in specific embodiments.

As examples, the respective elongated members may form an acute angle facing the major axis at a point at which the respective elongated members engage the internal member. At least one of the elongated members can include a base in the form of an oblique cone that engages the internal member, or in other embodiments the internal member can include at least one guide defining an opening generally directed toward the major axis, with at least one of the elongated members fixed to the internal member within the opening of the guide. A specific example has four elongated members, with pairs (e.g. a first and second and a third and fourth) symmetric with each other across the major axis, and pairs (e.g. the first and third and the second and fourth) symmetric with each other across the minor axis. The internal member may include at least one groove in the exterior surface, and the at least one groove may be generally parallel to the major axis. For instance, a plurality of grooves may be provided in the exterior surface, as with each groove being parallel to each other and one of the grooves being substantially along the major axis. Additionally or alternatively, the internal member can include at least one ridge in the interior surface, such as at least one ridge generally parallel to the major axis.

In other embodiments, a vascular closure system includes an internal member for anchoring or sealing against the inside wall of a blood vessel, and an exterior surface includes a groove that has a pair of facing surfaces meeting at a living hinge. The groove may follow the curvature of the exterior surface and be generally parallel to a major axis of the internal member, and at least one elongated member is attached to the interior surface of the internal member. Particular examples include having the groove substantially along the major axis of the internal member, and having a plurality of the grooves (e.g. arranged substantially parallel to each other and/or one of the grooves being substantially along the major axis of the internal member). The exterior surface can include at least one groove on one side of the major axis and at least one groove on the other side of the major axis. In such or other embodiments, the internal member can include at least one ridge on the interior surface, such as a ridge including a pair of facing surfaces joined at an apex. The ridge can overlie a groove, with the apex of the ridge and a living hinge of the groove over each other so that a line joining the apex and living hinge is perpendicular to the exterior surface of the internal member. Where the exterior surface includes a plurality of the grooves, and the interior surface includes a plurality of the ridges, each such ridge can overlie one of such grooves. The elongated member joins the internal member at one of the ridge(s), and/or a plurality of elongated members are fixed to the interior surface of the internal member, the elongated members arranged symmetrically across the major axis, with the elongated members non-orthogonal to the interior surface at a point at which the respective elongated members engage the internal surface, in particular embodiments.

A vascular closure and system is also disclosed that includes an internal member for anchoring or sealing against the inside wall of a blood vessel, with the internal member having a central region and a skirt region laterally outward of the central region and monolithically joined to the central region at a discrete bend region. Examples include a central region at least partially ellipsoidal and including a portion of the exterior surface and interior surface, and/or a skirt region including a portion of the exterior surface and interior surface each of which are substantially elliptically conical in form. A rim of the skirt region may be at a substantially constant distance from the bend region. The exterior surfaces of the central and skirt regions join at the bend region and form the exterior surface of the internal member, and the interior surfaces of the central and skirt regions join at the bend region and form the interior surface of the internal member. The internal member is adapted to initially bend substantially at or outside the bend region without substantially changing the shape of the central region. The internal member can be adapted to bend substantially at the bend region while the central region remains substantially ellipsoidal. A central elongated member is attached to the interior surface of the internal member, for example within the central region.

These and other features are shown in the particular examples described below.

DESCRIPTION OF THE ILLUSTRATED EMBODIMENTS

Figure 1:
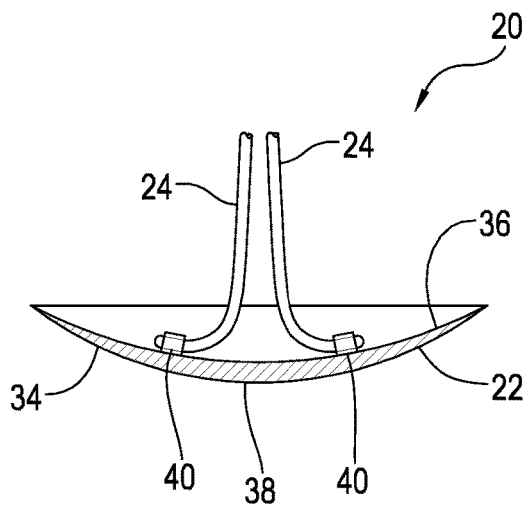
FIG. 1 is a part cross-sectional view of an embodiment of a device for closing holes in vessels or other tissue.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated embodiments, and such further applications of the principles of the disclosure as illustrated therein being contemplated as would normally occur to one skilled in the art to which the disclosure relates.

Referring now generally to the drawings, there are disclosed embodiments of an anchoring or sealing device 20, 120, 220, 320. Each such device includes respective internal members 22, 122, 222, 322 and one or more elongated members 24, 124, 224, 324 fixed to the internal members. Devices 20, 120, 220, 320 are particularly useful for closure of vascular wall openings that exceed 10 French in size, by providing better application and distribution of force. Throughout the following discussion, parts or features having the same final two numbers (e.g. 20 and 120) are similar or identical, and in many cases will be interchangeable with each other.

Device 20 (FIGS. 1-3) includes an internal member 22 designed for placement against the internal wall of a blood vessel V, and a plurality of elongated members 24 fixed to and extending proximally from member 22. The illustrated embodiment of member 22 is a substantially dome-shaped element, having a wall 30 defining a rim 32, an exterior convex surface 34 and an interior concave surface 36. Wall 30 can have a constant or varying thickness, for example in certain embodiments having a maximum thickness in the range of about 0.0050 inches to about 0.050 inches, and in a particular embodiment about 0.015 inches. In the illustrated embodiment, the substantially constant thickness of member 22 is at and/or between the connection(s) with elongated member 24, and the thickness decreases (e.g. uniformly) out to rim 32. Inner member 22 is part-spherical or part-spheroidal in an open, natural or unstressed state (e.g. FIG. 1), having a substantially circular or oval-shaped (e.g. elliptical) rim 32, with a major axis M and a perpendicular minor axis N. When unstressed, rim 32 is substantially in one plane in this embodiment, having little breadth. Exterior convex surface 34 and interior concave surface 36 are continuous in the illustrated embodiment, and surface 36 is open and unobstructed in an initial expanded configuration. In particular embodiments, surfaces 34 and 36 may have substantially the same radii, so that the overall thickness of wall 32 is substantially constant, or may have differing radii or centers of their respective radii, so that they intersect or approach each other at (and wall 32 thins toward) rim 32. A center point or line 38 may have a tangent plane at exterior surface 34 that is substantially parallel to the plane of rim 32.

Fixed to or molded as part of member 22, on surface 36, are respective holders or guides 40. In the illustrated embodiment, guides 40 include a wall or bar 42 attached at both ends to surface 36, forming an arch with a hole or passage 44. Passage 44 is directed generally toward or perpendicular to major axis M of member 22, and in the illustrated embodiment is substantially perpendicular to major axis M and/or parallel to minor axis N. That orientation focuses force applied through the elongated member 24 at points off (lateral) of the major axis, and in a direction to pull the sides of member 22, and separated by minor axis N (e.g. FIG. 3) toward major axis M.

Figure 2:
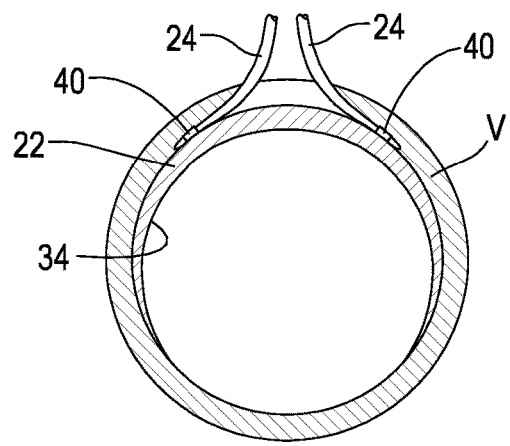
FIG. 2 is a part cross-sectional view of the embodiment of FIG. 1 in use within a vessel.

A respective elongated member 24 is fixed to each guide 40, so that attached pairs of elongated member 24 and guide 40 do not move with respect to each other. The attachment may be accomplished in any of a number of ways, such as by adhesive, interference fit, snap fit, or welding. The illustrated embodiment (FIG. 3) shows four separate elongated members 24, each of which is attached to a respective guide 40. Two guides 40 with respective elongated members 24 joined to them are shown in FIGS. 1-2, both on a particular side of the major axis of member 22. Two other elongated members 24 are shown, and their respective guides 40 are behind member 22 and not visible in the view of FIGS. 1-2. FIG. 2 show 2 in partial cross-section member 22 in place, pressed against the inside wall of a blood vessel V with elongated members 24 extending proximally from vessel V. The illustrated embodiment shows guides 40 symmetric with respect to each other across the major axis and minor axis of member 22, and in other embodiments such symmetry may be limited to only one or the other of the axes.

In the illustrated embodiments, elongated members 24 are firm and flexible, as a thin rod, wire or filament, e.g. of biocompatible suture or plastic material. In particular, elongated members 24 may be of the same solid material as member 22, to enable coalescence (e.g. by heat welding) or other firm engagement between them. In other embodiments, elongated members 24 may be very flexible and non-rigid, such as sutures or other filaments. In such embodiments, the elongated members 24 may include a tip piece (e.g. a snap insert or aglet) for attachment to member 22, if the elongated member is not directly embedded, glued or otherwise fixed to member 22. Elongated members 24, like member 22, are preferably of a biocompatible material that can be broken down by the body over time (e.g. over a period several days or weeks, to allow natural healing and closure to get underway) and absorbed or removed from the body.

Figure 3:
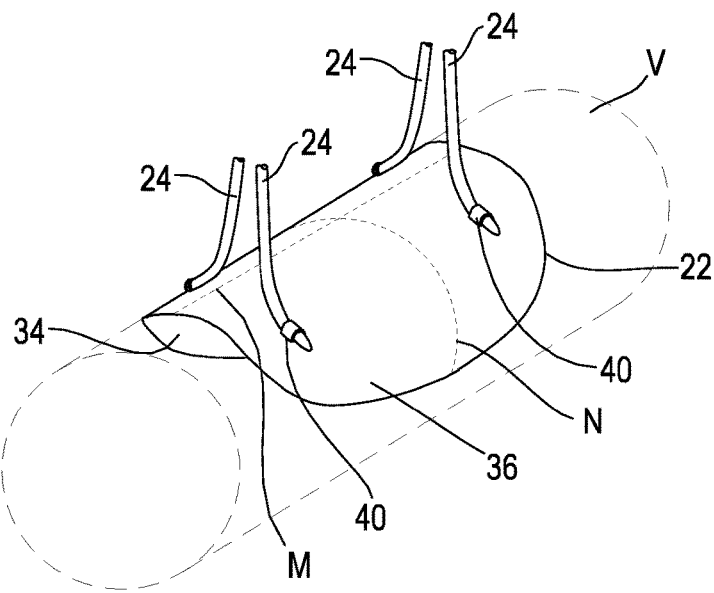
FIG. 3 is a perspective view of the embodiment of FIG. 1 in use within a vessel.

As seen in FIGS. 2-3, member 22 is shown inserted within a blood vessel V. In the illustrated embodiment, major axis M of member 22 is substantially parallel to the longitudinal axis of vessel V, and minor axis N is substantially parallel to the circumference of vessel V, although it will be understood that other orientations could potentially be used. Generally, device 20 (e.g. member 22 joined with member 24) is inserted into the vessel V through a hole to be closed. Device 20 is retracted until member 20 engages the inside wall, and member 20 bends or inverts to conform or fit against the inside of the vessel, covering the hole in the wall. Device 20 is then locked in position so that member 20 remains in position covering the hole, and member 24 extends away from the vessel. While this description has used the example of a bodily vessel, e.g. a blood vessel, it will be understood that embodiments may be used to cover or close other openings, such as fistulae or septal defects.

Member 22 fits or wraps around the circumference of the inside of the vessel, and in the illustrated embodiment wraps around at least 180 degrees of the circumference. Depending on the size of the hole to be closed and the location of the hole (i.e. the circumference of the particular vessel), member 22 may extend around substantially all or all of the vessel (e.g. about 360 degrees around the circumference) so that opposite edges of rim 32 of member 22 along minor axis N approach, abut or overlap with each other. It is believed that it is advantageous for member 22 to extend around between 180 and 300 degrees of the circumference, to ensure closure of the hole while minimizing narrowing of the vascular diameter. Guides 40 may engage the inner wall of vessel V, or if the hole is of sufficient size, may extend into the hole (e.g. adjacent or abutting an edge of the hole) when member 22 is pulled toward the vessel wall. By engaging the wall and/or a portion of the edge of the hole, guides 40 provide stability to member 22, helping prevent or limit migration of member 22 with respect to the hole.

Figure 4:
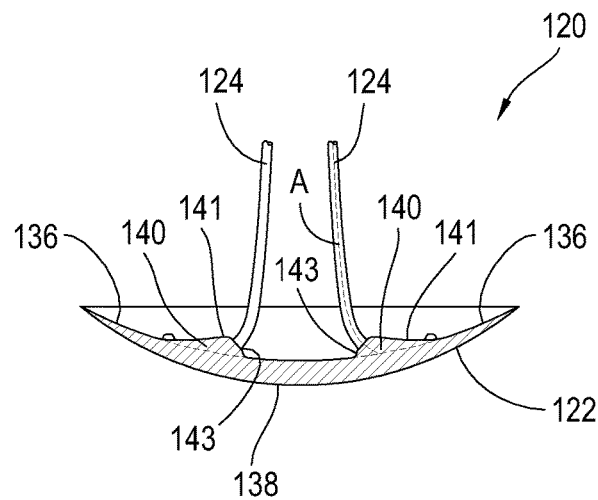
FIG. 4 is a part cross-sectional view of an embodiment of a device for closing holes in vessels or other tissue.
Figure 5:
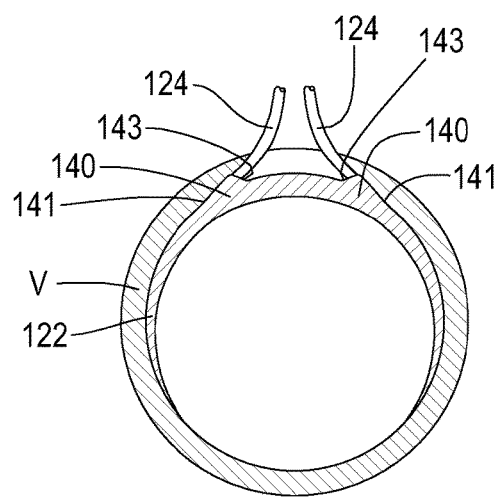
FIG. 5 is a part cross-sectional view of the embodiment of FIG. 4 in use within a vessel.
Figure 6:
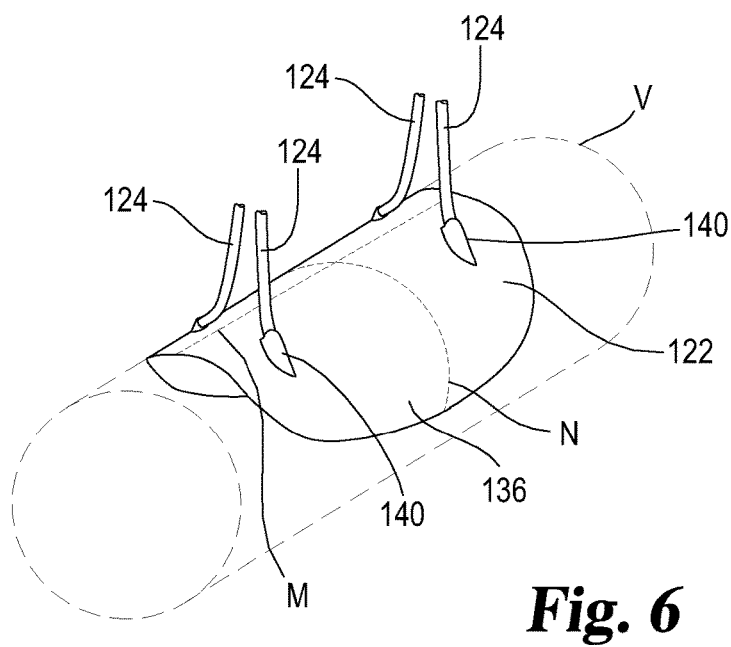
FIG. 6 is a perspective view of the embodiment of FIG. 4 in use within a vessel.
Figure 7:
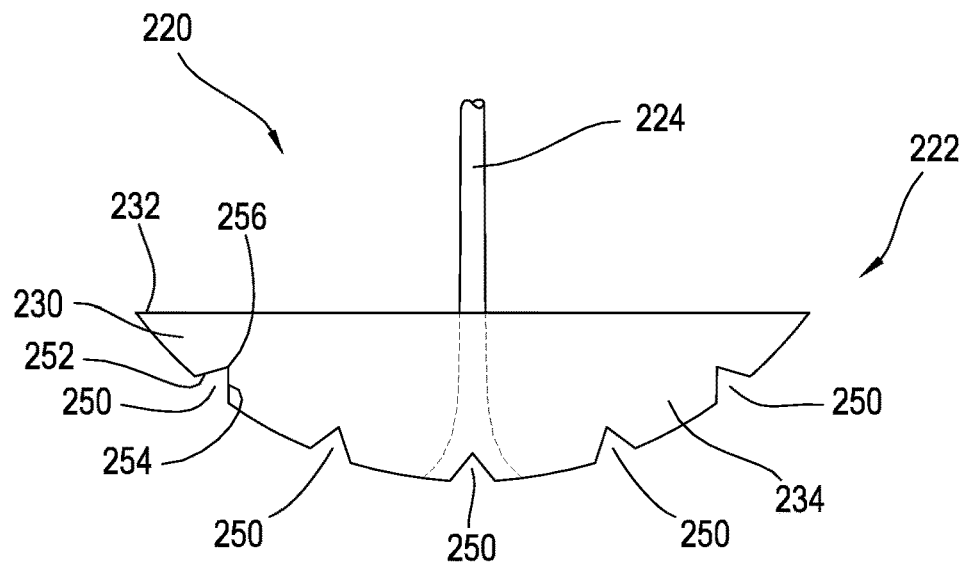
FIG. 7 is a side view of an embodiment of a device for closing holes in vessels or other tissue.
Figure 8:
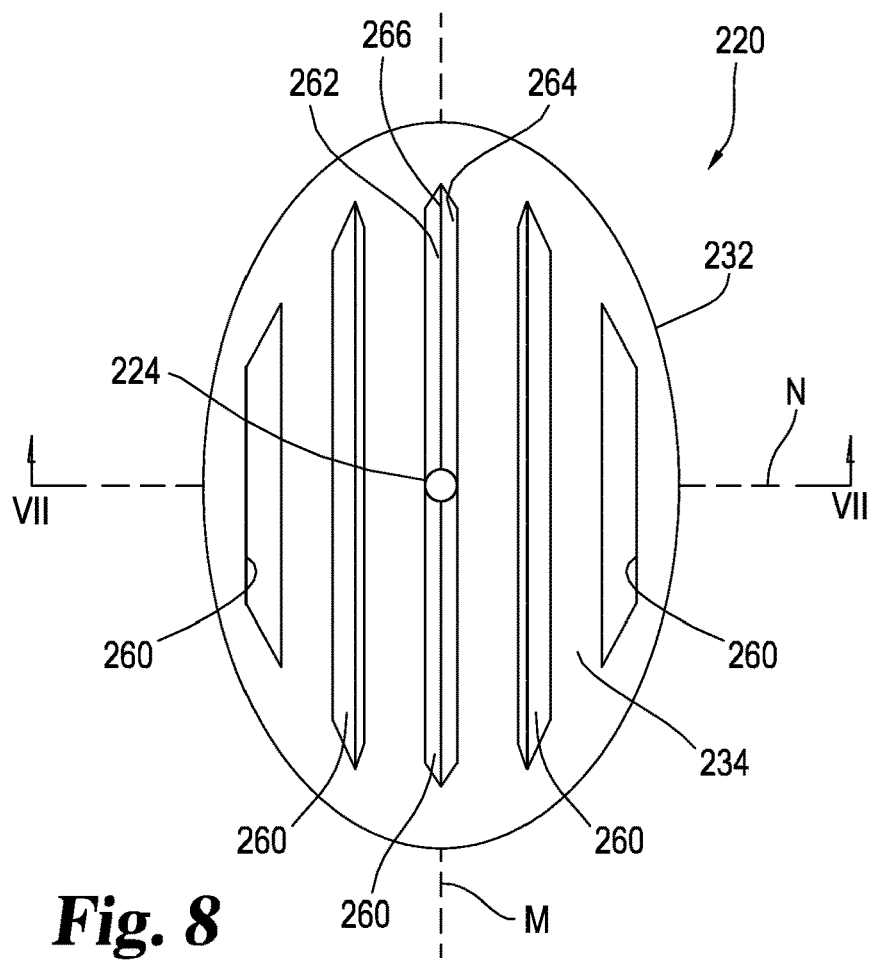
FIG. 8 is a top view of the embodiment of FIG. 7.
Figure 9:
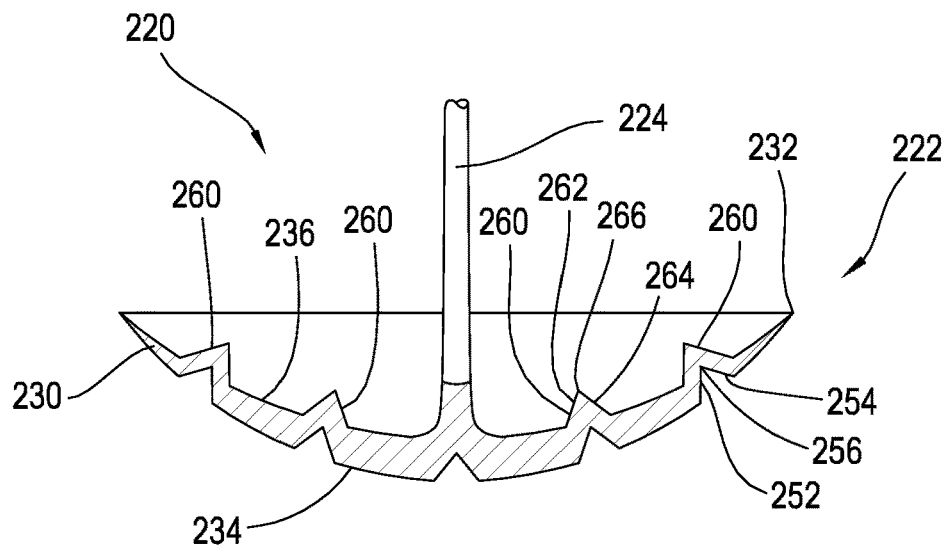
FIG. 9 is a part cross-sectional view of the embodiment of FIG. 7, taken along the lines VII-VII in FIG. 8 and viewed in the direction of the arrows.
Figure 10:
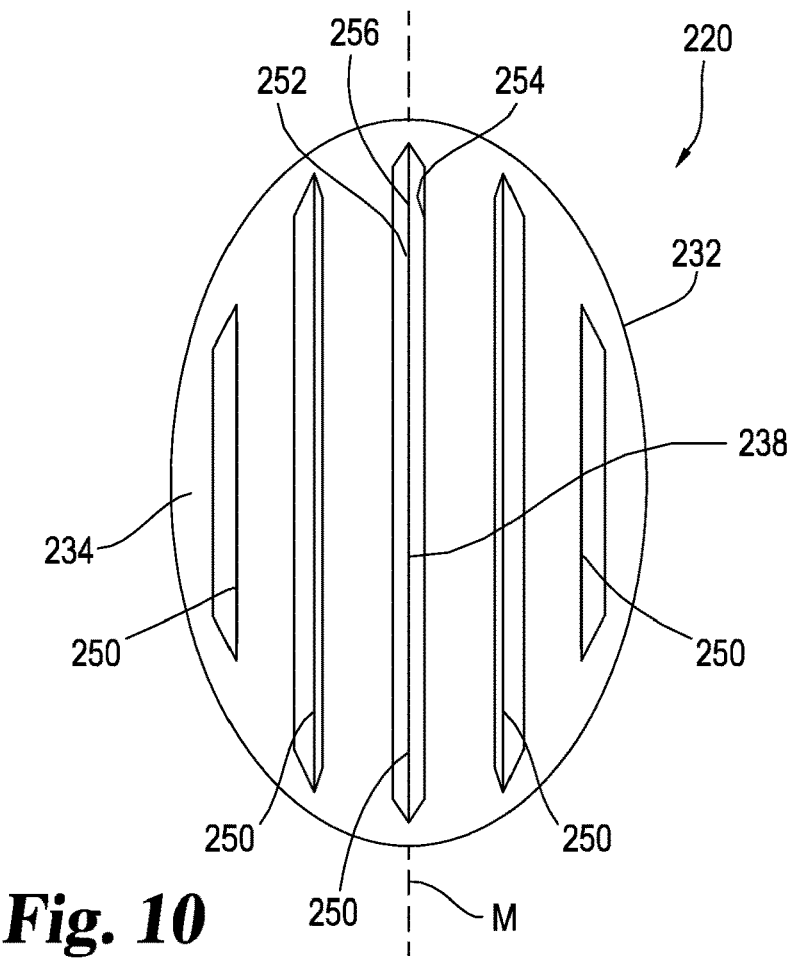
FIG. 10 is a bottom view of the embodiment of FIG. 7.

In FIGS. 4-6, there is shown an internal member 122 having a series of elongated members 124 extending proximally from it. Internal member 122 is an ellipsoid (e.g. oval or spheroid) piece very similar to member 22 discussed above, and therefore the features of member 122 identical to those discussed above with respect to member 22 will not be repeated here. As with device 20, this embodiment of device 120 has elongated members 124 that are fixed to member 122. However, in this embodiment, no guides are provided. Rather, each elongated member 124 has a specially configured base portion 140 that joins the elongated member 124 with member 122 in a monolithic whole. Base portion 140 enlarges from the diameter of elongated member 124 toward surface 136 of member 122. Widened base portion 140 in this embodiment may be thought of as a cone that is not orthogonal with the portion of surface 136 to which it joins, and in that sense is not isomorphic. Thus, a side 141 of base portion 140 that generally faces or leads to the outer rim of member 122 forms an obtuse angle with a smooth curve with surface 136 into which it runs, and a side 143 of base portion 140 that generally faces or leads to the center or major axis of member 122 forms an acute angle with surface 136 into which it runs. A central axis A through an elongated member 124 is oblique to the curve of surface 136, and specifically so that axis A has an acute angle with the curve of surface 136 that faces the center 138 or major axis M.

The orientation and positioning of guides 40 and that of base members 140 moves the location of application of pulling force on members 22, 122 to the side, i.e. laterally off of axes M and N and closer to the edge or rim, and orients the pulling force toward major axis M and parallel to axis N in this embodiment. As the user retracts members 22, 122 toward and against the wall of vessel V using elongated members 24, 124, tension increases in elongated members 24, 124. That tension is transmitted to member 22, 122, pulling member 22, 122 against the wall. Guides 40 of member 22 and base members 140 of member 122 effectively turn or re-orient the tension in elongated members 24, 124 from substantially perpendicular to member 22, 122 to a direction toward rim 32, 132, so as to pull the sides of member 22, 122 more directly toward the vascular opening and the wall surrounding it. The elongated members 24, 124 are maintained close to or along the wall at least in part, which helps prevent pulling members 22, 122 through the hole. These embodiments of devices 20, 120 can increase wall opposition forces toward the edge of the dome by placing the elongated members (e.g. suture, filament or stem members) closer to the edge of the dome. The guiding or re-orientation features force the elongated members to hug the underside of the dome and the curvature of the vessel.

As with device 20, the illustrated embodiment of device 120 includes four elongated members 124 and their respective base portions 140. Base portions 140 are located symmetrically with respect to each of the major and minor axes in this embodiment. Other numbers of elongated members 24, 124 may be used in other embodiments. For example, an even number of elongated members 24, 124 may be attached to a member 22, 122, with members 24, 124 positioned across from each other with respect to major axis M (e.g. a line joining adjacent members 24, 124 or base portions or guides 40, 140 may be substantially perpendicular to axis M). Use of device 120 is also substantially or identically as described above with respect to device 20.

Referring now to FIGS. 7-10, there is shown an embodiment of a closure device 220 having an internal anchoring or sealing member 222 and an elongated member 224. As seen in the drawings, elongated member 224 is attached at or approximately at the center 238 of member 222. It will be understood, however, that off-centered positioning (such as is discussed above) may be used.

The illustrated embodiment of internal member 222 is very similar to member 22. Member 222 is a substantially dome-shaped element, having a wall 230 defining a rim 232, an exterior convex surface 234 and an interior concave surface 236. Internal member 222 is ellipsoidal in an open, natural or unstressed state (e.g. FIG. 7), having a substantially circular or oval-shaped (e.g. elliptical) rim 232. Rim 232 is substantially in one plane in this embodiment, having little breadth.

Exterior convex surface 234 in this embodiment includes a set of longitudinal grooves 250, each having respective facing planar surfaces 252, 254 that come together at a joint 256. In this context, "longitudinal" means along the long dimension (axis M) of member 222, and the illustrated example shows grooves 250 linear and substantially parallel to the major axis of member 222. The example includes five grooves 250, with a center groove 250 directly beneath elongated member 224 and the other grooves 250 arranged symmetrically to either side. It will be understood that such a set may include one or more grooves 250 in the same or other arrangements. Each joint 256 acts as a living hinge, allowing its respective surfaces 252, 254 to come together when member 222 is pulled toward or against the vascular wall.

Figure 11:
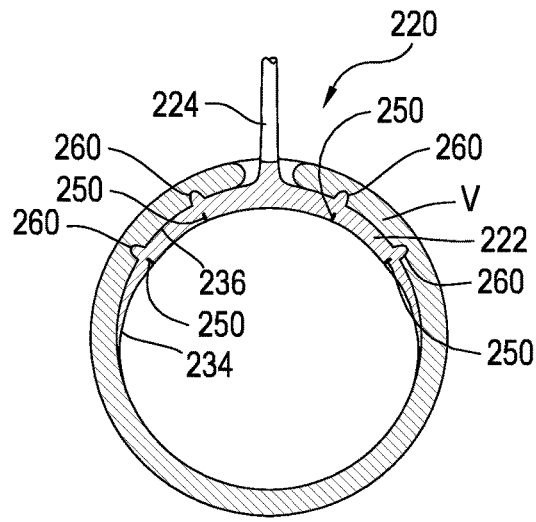
FIG. 11 is a part cross-sectional view of the embodiment of FIG. 7 in use within a vessel.

Interior concave surface 236 in this embodiment is open and unobstructed in an initial expanded (natural or unstressed) configuration, and includes a set of longitudinal ridges 260. The illustrated example features each ridge 260 generally positioned atop of or opposite a respective groove 250, i.e. a set of five ridges 260. Each ridge 260 in this embodiment includes respective planar side surfaces 262, 264, with an apex 266 between them that may be rounded or relatively pointed. As with grooves 250, in the context of ridges 260 the use of "longitudinal" suggests that the ridges are substantially parallel to each other and to the major axis M of member 222, and thus are also at least substantially parallel to the lumen at discrete locations around the circumference of the vessel when implanted (e.g. FIG. 11). As illustrated, in embodiments having a central ridge 260 (e.g. one along the major axis M of member 222) and an elongated member 224 attached in the center or along the major axis M, elongated member 224 and the central ridge 260 will intersect, and in the illustrated embodiment elongated member 224 extends on each side of apex 266 of the central ridge 260. A set of ridges 260 may include one or more such ridges, arranged as illustrated or in other configurations. Ridges 260 positioned and oriented as illustrated provide strength to the living hinge operation of grooves 250, as the thickness of member 220 between apex 266 and joint 256 is not reduced. As member 222 engages the wall of vessel V and is pulled further, grooves 250 narrow or reduce. That is, surfaces 252, 254 approach each other, pivoting around hinge or joint 256. Surfaces 262, 264 also fold toward each other around apex 266, reducing the angle between surfaces 262, 264, and in some embodiments bringing at least a portion of surfaces 262 an 264 toward or to a parallel condition.

In this embodiment, with ridges 260 and grooves 250, it is understood that device 220 can be made with less material, yet provide as good or better structural function and support. Ridges 260 and grooves 250 in the illustrated embodiment create a wavy corrugated pattern. Grooves 250 act as weak points so member 222 is easier to invert. Ridges 260 act as reinforcing ribs when member 222 inverted, and so member 222 is easier to place while having more strength in its inverted position due to the reinforcing ribs. As grooves 250 close during placement, the opposing surfaces can engage to press against and support each other, leaving an essentially seamless exterior when device 220 is implanted. Grooves 250 provide for a decrease in the dimension of device 220 as it is placed, while still covering the tissue opening, and ridges 260 can engage at least some of the tissue surface. Further, ridges 260 provide reinforcement to of member 222, enabling a greater surface area to contact the vessel wall.

Although the embodiment shown in FIGS. 7-10 include both grooves 250 and ridges 260, it will be understood that other embodiments may have a set of groove(s) or a set of ridge(s) rather than both. Further, embodiments having both grooves and ridges as disclosed may have them offset from each other, rather than opposite each other as shown. It is believed that the living hinge operation of grooves 250 will be assisted if ridges 260 are opposite them.

Figure 12:
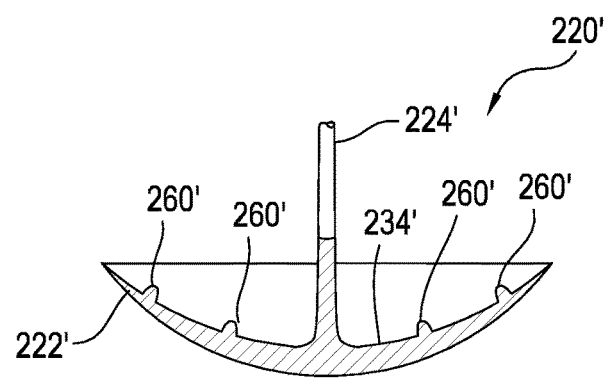
FIG. 12 is a part cross-sectional view of an embodiment similar to the embodiment of FIG. 7.
Figure 13:
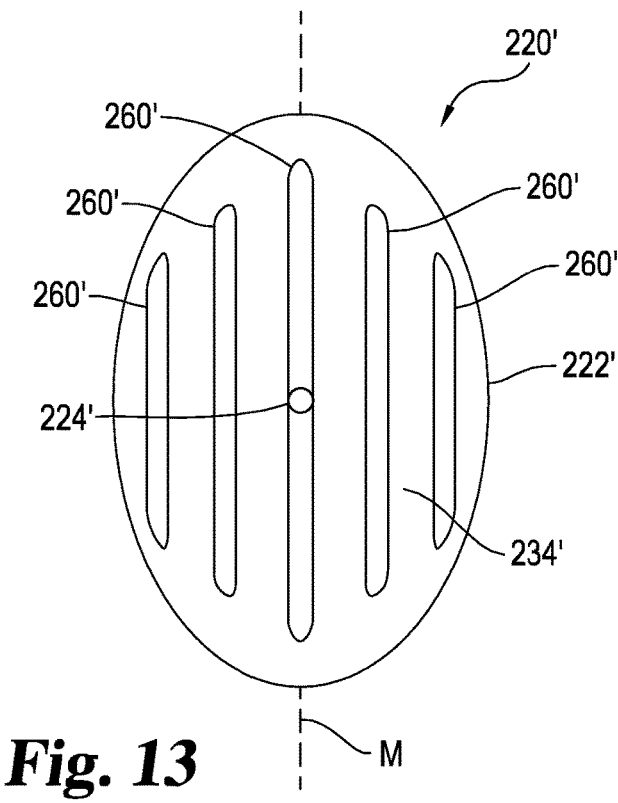
FIG. 13 is a top view of the embodiment of FIG. 12.

As seen in FIGS. 12-13, embodiments of a device 220' with only a series of ridges or ribs 260' is shown. Ribs 260' are arranged substantially as ridges 260 are, e.g. longitudinal or parallel to a major axis M along at least a portion of internal surface 234' of member 222'. Elongated member 224' engages member 222' at one of the ribs 260' in this embodiment. As the device 220' is deployed within the vessel, with axis M at least substantially parallel to the lumen of the vessel, ribs 260' are also at least substantially parallel to the lumen, and are at discrete locations around the circumference of the vessel. They thus do not make member 220' harder to bend into shape when deployed. Ribs 260' are shown as solid in this embodiment. As with ridges 260, ribs 260' may have a number of cross-sectional shapes or configurations, such a substantially triangular with pointed or curved apexes. Ribs 260' provide reinforcement for member 222', particularly toward the edge of member 222', which is expected to help member 222' hug the vessel wall.

Referring now generally to FIGS. 14-17, there is shown an embodiment of a vascular closure device 320, that includes an internal anchoring or sealing member 322 and at least one elongated member 324. In this embodiment, member 322 is generally in the form of an ellipsoidal dome with a central button or bump portion 380 and a surrounding annular skirt portion 382. Between button 380 and skirt portion 382 is a bending zone or living hinge 384, providing a location for member 322 to initially bend skirt portion 382 with respect to bump portion 380. An external surface 334 and an internal surface 336 of member 322 extend through each of the bump 380 and skirt 382.

Figure 14:
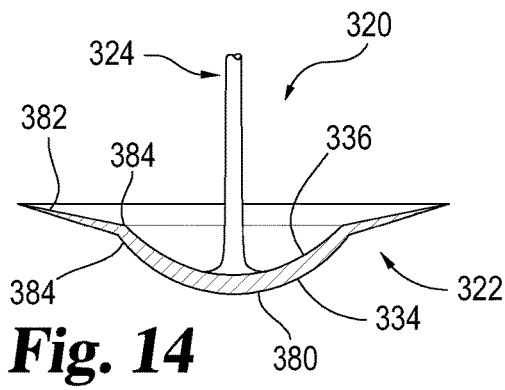
FIG. 14 is a part cross-sectional view of an embodiment of a device for closing holes in vessels or other tissue.
Figure 15:
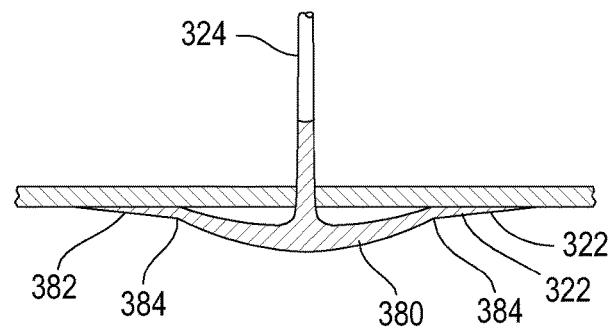
FIG. 15 is a part cross-sectional view of the embodiment of FIG. 14 with tension pressing it against a substantially flat surface, such as a tissue surface.
Figure 16:
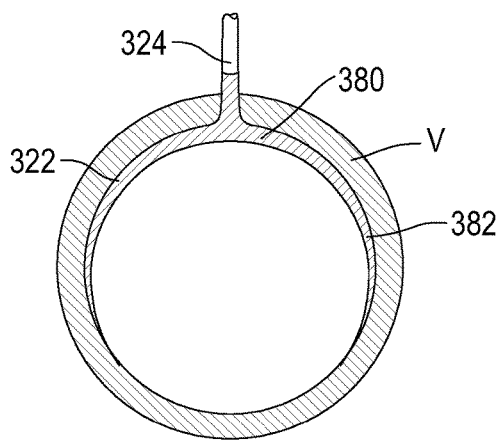
FIG. 16 is a part cross-sectional view of the embodiment of FIG. 14 in use within a vessel.
Figure 17:
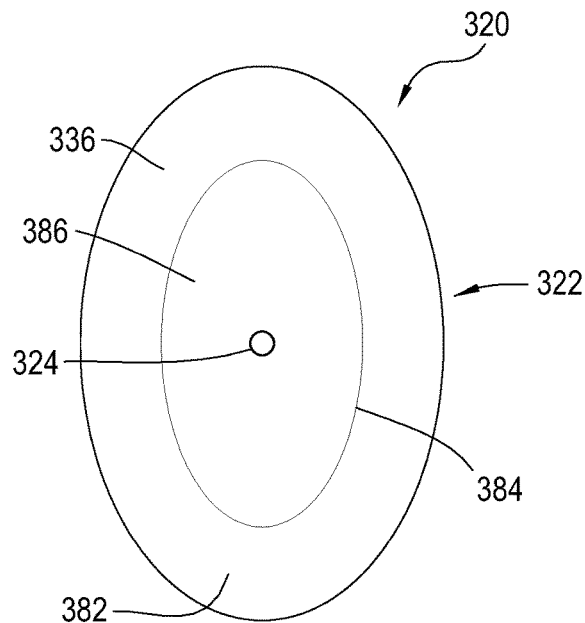
FIG. 17 is a top view of the embodiment of FIG. 14.

Bump portion 380 is configured as a portion of an ellipsoid, and as seen in FIG. 14 may have a cross-sectional shape that is substantially circular. Each of internal surface 336 and external surface 334 in bump 380 has a rounded (e.g. circular) cross-section. The thickness of bump 380 (i.e. the distance between internal surface 336 and external surface 334 in bump portion 380) is greatest in this embodiment at the center or along major axis M, and thins as it approaches hinge 384. Elongated member 324 attaches to bump 380 at its part of interior surface 336, and is centrally located in the illustrated embodiment. It will be understood that one or more elongated members 324 may be used, and the attachment of member(s) 324 to bump 380 may be accomplished by any of the methods noted herein, including formation of member(s) 324 and member 322 as a monolithic unit.

Skirt portion 382 is configured as a portion of a cone attached to bump 380 at hinge zone 384. In the illustrated embodiment, when viewed in cross section the internal surface 336 and external surface 334 in skirt portion 382 are each flat, and narrow toward a thin or pointed rim 332. Hinge portion 384 joins skirt portion 382 to bump portion 380, and in that respect is of (or varies between) approximately the largest width of skirt 382 and the smallest width of bump 380. In cross-section, the illustrated embodiment's external surface 334 is substantially convex in bump 380, but reverses to concave or inward-bending at hinge 384, extending substantially linearly along skirt 382. Similarly, internal surface 336 is substantially concave in bump 380, reversing to convex or outward-bending at hinge 384 and extending substantially linearly along skirt 382. Member 322 may be sized and configured with hinge portion 384 having a distance from elongated member 324 such that the area within hinge 384 is larger than the dimension of the tissue hole to be closed, i.e. when member 322 is implanted, hinge 384 will surround most or all of the hole to be closed.

Device 320 is used in essentially the same way as devices 20, 120, 220 and 220' discussed above. Once inserted into a vessel through an opening in the vessel wall, member 322 is pulled against the vessel wall. As rim 322 engages the wall, hinge portion 384 and/or skirt portion 382 bend toward conformance with the wall. Bump portion 380 does not tend to bend initially due to its geometric configuration with respect to hinge 384 and skirt 382. Stress applied to rim 322 that bends skirt 382 and/or hinge 384 has less or no effect on bump 380 at least because of the convex shape of bump 380, in which the portion of bump 380 adjoining hinge 384 is parallel (or more parallel) to the pulling force exerted on device 320 as compared to the orientation of skirt 382. When skirt 382 and hinge 384 are bent or flexed so that they are substantially fully against the vessel or other tissue wall, bump 380 may still remain convex and extend out from the wall. Further pulling force on member 322 can quickly flatten or at least partially invert bump 380 so that substantially all of internal surface 336 is against the wall or facing the hole in the vessel or tissue wall to be closed. Such embodiments use this quick transition from concave to convex of inner surface 336 in bump portion 380 to increase the wall opposition force of member 322. It also allows member 322 to bend from three points instead of one or two, which may increase its ability to achieve greater curvature. The additional pulling force needed to flatten bump 380 provides further pressure between hinge 384 and the tissue wall, so as to provide a more secure seal between member 322 and the tissue.

While the embodiments have been illustrated and described in detail in the drawings and foregoing description, the same is to be considered as illustrative and not restrictive in character, it being understood that only particular embodiments have been shown and described and that all changes and modifications that come within the spirit of the disclosure are desired to be protected. It will be understood that features or attributes noted with respect to one or more specific embodiments may be used or incorporated into other embodiments of the structures and methods disclosed. The term "ellipsoid" and its variants as used herein are generally intended to mean rounded three-dimensional structures, shells or domes, or part of one, such as those resulting from the turning of an ellipse (including a circle) around an axis, and includes spherical or part-spherical shapes.

What is claimed is:

1. A vascular closure system, comprising:
    an internal member for anchoring or sealing against an inside wall of a blood vessel, the internal member being at least partially ellipsoidal with a major axis and a minor axis, and having an exterior surface for facing away from the inside wall and an interior surface for facing the inside wall, the internal member including an elongated member for use in placement of the internal member,
    the internal member having a central region and a skirt region laterally outward of the central region and monolithically joined to the central region at a hinge, the elongated member being fixed with respect to the central region and not extending through the interior surface or the exterior surface of the central region, the central region being at least partially ellipsoidal and including a portion of the exterior surface and the interior surface, the skirt region including a portion of the exterior surface and the interior surface each of which are substantially elliptically conical in form, the skirt region having a rim at a substantially constant distance from the hinge, the exterior surfaces of the central and skirt regions joining at the hinge and forming the exterior surface of the internal member, the interior surfaces of the central and skirt regions joining at the hinge to form an angle in the interior surface of the internal member, wherein in an initial unstressed configuration the exterior surface is convex in the central region, inward-bending at the hinge, and linear in cross-section along the skirt region, and the interior surface is concave in the central region, convex at the hinge, and linear in cross-section along the skirt region, wherein the internal member is adapted to initially bend substantially at or outside the hinge without substantially changing the shape of the central region, and wherein the internal member has an area inside of the hinge which is configured to be greater than an area of a hole in the inside wall over which the internal member will be placed.

2. The system of claim 1, wherein the elongated member is attached centrally to the interior surface of the internal member.

3. The system of claim 1, further comprising a plurality of the elongated members fixed to the interior surface of the internal member.

4. The system of claim 3, wherein
    the plurality of elongated members are arranged symmetrically across the major axis, wherein the plurality of elongated members are non-orthogonal to the interior surface at respective points at which the plurality of elongated members engage the internal member.

5. The system of claim 4, wherein the plurality of elongated members each form an acute angle facing the major axis at the respective points at which the plurality of elongated members engage the internal member.

6. The system of claim 4, wherein at least one of the plurality of elongated members includes a base in the form of an oblique cone that engages the internal member.

7. The system of claim 4, wherein the internal member includes at least one guide defining an opening generally directed toward the major axis, and wherein at least one of the plurality of elongated members is fixed to the internal member within the opening of the guide.

8. The system of claim 4, wherein the plurality of elongated members includes at least first, second, third and fourth elongated members, and wherein the first and second elongated members are symmetric with each other across the major axis, the third and fourth elongated members are symmetric with each other across the major axis, the first and third elongated members are symmetric with each other across the minor axis, and the second and fourth elongated members are symmetric with each other across the minor axis.

9. The system of claim 1, wherein the hinge is a living hinge.

10. The system of claim 1, wherein the central region has a central point on the exterior surface having a tangent plane, and wherein in the initial unstressed configuration, the rim is in a plane parallel to the tangent plane, and the interior surface at the hinge is between the plane of the rim and the tangent plane.

11. The system of claim 1, wherein the internal member has a first tensioned configuration after application of an amount of force in which the skirt region is flexed so that the skirt region is configured to press against the inside wall but the exterior surface and interior surface of the central region remain respectively convex and concave, and a second tensioned configuration to be achieved after the first tensioned configuration in which the central region is at least partially inverted so that the interior surface in the central region is configured to engage the inside wall and the exterior surface in the central region is concave.

12. The system of claim 1, wherein the internal member is adapted to remain in place with respect to the blood vessel after a medical procedure is completed.

13. The system of claim 12, wherein the internal member is of biocompatible material that can be broken down in vivo over time to allow natural healing and closure to get underway.

14. The system of claim 1, wherein the elongated member does not have a longitudinal lumen.

15. The system of claim 14, wherein the elongated member is one of a thin rod, wire or filament.

* * * * *